United States Patent
Leroux et al.

(10) Patent No.: US 6,478,822 B1
(45) Date of Patent: Nov. 12, 2002

(54) SPHERICAL SPINAL IMPLANT

(75) Inventors: Clayton G. Leroux, Fairview Park, OH (US); Robert S. Biscup, Chagrin Falls, OH (US)

(73) Assignee: Spineco, Inc., Fairview Park, OH (US)

( * ) Notice: Subject to any disclaimer, the term of this patent is extended or adjusted under 35 U.S.C. 154(b) by 0 days.

(21) Appl. No.: 09/865,114

(22) Filed: May 24, 2001

Related U.S. Application Data (60) Provisional application No. 60/277,038, filed on Mar. 20, 2001.

(51) Int. Cl.[7] .................................................. A61F 2/44
(52) U.S. Cl. ..................................................... 623/17.14
(58) Field of Search ........................... 623/16.11, 17.11, 623/17.14, 17.16

(56) References Cited

U.S. PATENT DOCUMENTS

| | | | |
|---|---|---|---|
| 4,349,921 A | 9/1982 | Kuntz | |
| 4,714,469 A | 12/1987 | Kenna | |
| 4,834,757 A | 5/1989 | Brantigan | |
| 4,878,915 A | 11/1989 | Brantigan | |
| 4,936,848 A | * 6/1990 | Bagby | 606/61 |
| 4,961,740 A | 10/1990 | Ray et al. | |
| 5,059,193 A | 10/1991 | Kuslich | |
| 5,192,327 A | 3/1993 | Brantigan | |
| 5,258,031 A | 11/1993 | Salib et al. | |
| 5,306,307 A | 4/1994 | Senter et al. | |
| 5,425,772 A | 6/1995 | Brantigan | |
| 5,425,773 A | 6/1995 | Boyd et al. | |
| 5,562,738 A | 10/1996 | Boyd et al. | |
| 5,607,424 A | 3/1997 | Tropiano | |
| 5,609,635 A | 3/1997 | Michelson | |
| 5,645,596 A | * 7/1997 | Kim et al. | 623/17.16 |
| 5,658,337 A | 8/1997 | Kohrs et al. | |
| 5,674,296 A | * 10/1997 | Bryan et al. | 606/61 |
| 5,743,918 A | 4/1998 | Calandruccio et al. | |
| 5,766,252 A | 6/1998 | Henry et al. | |
| 5,782,832 A | 7/1998 | Larsen et al. | |
| 5,782,919 A | 7/1998 | Zdeblick et al. | |
| 5,888,224 A | 3/1999 | Beckers et al. | |
| 5,888,226 A | * 3/1999 | Rogozinski | 623/17.16 |
| 5,888,227 A | 3/1999 | Cottle | |
| 5,895,428 A | 4/1999 | Berry | |
| 6,019,792 A | 2/2000 | Cauthen | |
| 6,059,829 A | 5/2000 | Schläpfer et al. | |
| 6,080,158 A | 6/2000 | Lin | |
| 6,113,638 A | 9/2000 | Williams et al. | |
| 6,179,874 B1 | 1/2001 | Cauthen | |
| 6,264,695 B1 | * 7/2001 | Stoy | 623/17.16 |
| 6,383,519 B1 | * 5/2002 | Sapieszko et al. | 424/401 |

OTHER PUBLICATIONS

Application Ser. No. 09/494,645, filed Jan. 31, 2000, entitled "Spinal Fusion Implant."

* cited by examiner

*Primary Examiner*—Corrine McDermott
*Assistant Examiner*—Will H Matthews
(74) *Attorney, Agent, or Firm*—Fay, Sharpe, Fagan, Minnich & McKee (57) ABSTRACT

An improved prosthetic implant for forming a support structure between adjoining vertebrae in a spinal column. The prosthetic implant includes a generally spherical or ellipsoidal body that at least partially engages a surface of an adjacent vertebrae. The generally spherical or ellipsoidal body can include an opening to receive packing material such as medicine, human tissue and the like. The generally spherical or ellipsoidal body can include a stabilizer to at least partially limit the movement of the prosthetic implant between two vertebrae.

89 Claims, 5 Drawing Sheets

SPHERICAL SPINAL IMPLANT

This application claims priority on co-pending U.S. Provisional Application Ser. No. 60/277,038, filed Mar. 20, 2001, entitled "Spherical Spinal Implant."

The present invention pertains to prosthetic implants, and more particularly to inner body spinal prosthetic implants to fuse two or more vertebrae together, and even more particularly to inner body spinal prosthetic implants that provide a substitute for an intervertebral disc and/or that provide a flexible spacer between two vertebrae.

INCORPORATION BY REFERENCE

U.S. Provisional Application Ser. No. 60/277,038, filed Mar. 30, 2001, entitled "Spherical Spinal Implant" is incorporated by reference. Also incorporated herein by reference is U.S. patent application Ser. No. 09/494,645, filed Jan. 31, 2000 entitled "Spinal Fusion Implant."

BACKGROUND OF THE INVENTION

The human spine is made up of a column of thirty-three bones and their adjoining structures. The vertebrae near the head are known as the presaccral vertebrae which are separate bones capable of individual movement. The bodies of these vertebrae are connected by anterior and posterior ligaments and by discs of fibrocartilage generally known as intervertebral discs. These discs are positioned between opposite faces of adjacent vertebral bodies. This column of vertebrae and intervertebral discs form a central axis that supports the head and torso. These vertebrae also enclose an opening through which the spinal cord passes therebetween.

The presaccral vertebrae are normally held in position to one another by the intervertebral discs, ligaments and musculature of the body. These vertebrae move relative to adjacent vertebrae thus permitting the head to be turned relative the body and providing a wide range of flexibility to the spine.

One of the most costly health problems in society involves back pain and pathology of the spine. These problems can affect individuals of all ages and can result in great suffering to victims. Back pain can be caused by several factors such as congenital deformities, traumatic injuries, degenerative changes to the spine, and the like. Such changes can cause painful excessive motion, or collapse of a motion segment resulting in the contraction of the spinal canal and compressing the neural structures causing debilitating pain, paralysis or both, which in turn can result in nerve root compression or spinal stenosis.

Nerve conduction disorders can also be associated with intervertebral discs or the vertebrae themselves. One such condition is herniation of the intervertebral disc, in which a small amount of tissue protrudes from the sides of the disc into the foramen to compress the spinal cord. A second common condition involves the development of small bone spurs, termed osteophytes, along the posterior surface of the vertebral body, again impinging on the spinal cord.

Upon identification of these abnormalities, surgery may be required to correct the problem. For those problems associated with the formation of osteophytes or herniations of the intervertebral disc, one such surgical procedure is intervertebral discectomy. In this procedure, the involved vertebrae are exposed and the intervertebral disc is removed, thus removing the offending tissue or providing access for the removal of the bone osteophytes. A second procedure, termed a spinal fusion, may then be required to fix the vertebrae together to prevent movement and maintain a space originally occupied by the intervertebral disc. Although this procedure may result in some minor loss and flexibility in the spine, due to the relatively large number of vertebrae, the minor loss of mobility is typically acceptable.

During a spinal fusion following a discectomy, a prosthetic implant or spinal implant is inserted into the intervertebral space. This prosthetic implant is often a bone graft removed from another portion of the patient's body, termed an autograph. The use of bone taken from the patient's body has the important advantage of avoiding rejection of the implant, but has several shortcomings. There is always a risk in opening a second surgical site in obtaining the implant, which can lead to infection or pain for the patient, and the site of the implant is weakened by the removal of bony material. The bone implant may not be perfectly shaped and placed, leading to slippage or absorption of the implant or failure of the implant to fuse with the vertebrae.

Other options for a graft source of the implant are bone removed from cadavers, termed allograft, or from other species, termed a xenograft. In these cases, while there is the benefit of not having a second surgical site as a possible source of infection or pain, there is increased difficulty of the graft rejection and the risk of transmitting communicable diseases.

An alternative approach is using a bone graft or. using a manufactured implant made of a synthetic material that is biologically compatible with the body and the vertebrae. Several compositions and geometries of such implants have been utilized, ranging from simple blocks of material to carefully shaped implants, with varying success.

There has been an extensive number of attempts in developing an acceptable prosthetic implant that can be used to replace an intervertebral disc and yet maintain the stability of the intervertebral disc spaced between adjacent vertebrae, at least until complete arthrodesis is achieved. These prosthetic implants have taken many forms. While many types of synthetic prosthetic devices have been proposed, the success ratio has been low and the surgical procedures have been complicated and often traumatic to the patient.

One of the more prevailing designs of these prosthetic implants takes the form of a cylindrical implant. These types of prosthetic implants are represented by Brantigan U.S. Pat. No. 4,878,915 and Ray U.S. Pat. No. 4,961,740. In these cylindrical implants, the exterior portion of the cylinder can be threaded to facilitate insertion of the prosthetic device. Some. of these prosthetic implants are designed to be pounded into the intervertebral disc space and the vertebral end plates. These types of devices are represented in Brantigan U.S. Pat. No. 4,834,757 and Brantigan U.S. Pat. No. 5,192,327. The Brantigan and Ray patents all disclose prosthetic implants wherein the transverse cross-section of the implant is constant throughout the length of the implant and is typically in the form of a right circular cylinder.

Other prosthetic implants have been developed that do not have a constant cross-section. For instance, the patent to Kenna U.S. Pat. No. 4,714,469 shows a hemispherical implant with elongated protuberances that project into the vertebral end plate. The implant of Bagby U.S. Pat. No. 4,936,848 is in the form of a sphere which is positioned between the centrums of the adjacent vertebrae.

The various prosthetic implants can be generally divided into two basic categories, namely solid implants and implants designed to encourage bone ingrowth. Solid implants are represented by U.S. Pat. Nos. 4,878,915 and 4,349,921. The remaining patents discussed above include some aspect that permits bone to grow across the implant. It has been found that devices which promote natural bone ingrowth achieve a more rapid and stable arthrodesis. These implants are typically filled with autologous bone prior to insertion into the intervertebral disc space. These implants typically include apertures which communicate with openings in the implant, thereby providing a path for tissue growth between the vertebral end plate and the bone or bone substitute within the implant. In preparing the intervertebral disc space for a prosthetic implant, the end plates of the vertebrae are preferably reduced to bleeding bone to facilitate tissue growth within the implant.

A number of difficulties still remain with the many prosthetic implants currently available. While it is recognized that hollow implants which permit bone ingrowth in the bone or bone substitute within the implant is an optimum technique for achieving fusion, most of these devices have difficulty achieving this fusion, at least without the aid of some additional stabilizing device, such as a rod or plate. Moreover, some of these devices are not structurally strong enough to support the heavy loads applied at the most frequently fused vertebral levels, mainly those in the lower lumbar spine.

In view of the present state of technology related to prosthetic implants, there is a continued need for new implant designs that optimize the bone ingrowth capabilities and are strong enough to support the vertebrae until arthrodesis occurs, maintains or restores the normal spinal anatomy at the instrumented segment, and/or exhibits reduced slippage when inserted between vertebrae and diminishes the occurrence of nerve pinching.

SUMMARY OF THE INVENTION

The present invention pertains to an improved implant, and more particularly to an improved prosthetic implant for insertion between one or more vertebrae and a method for inserting the prosthetic implant between one or more vertebrae.

In accordance with the principal feature of the present invention, there is provided a prosthetic implant that is formed of a biologically compatible material for use in humans. The prosthetic implant is shaped and sized for insertion between two vertebrae. In one specific embodiment, the prosthetic implant is designed to be placed in the intervertebral disc space that was formerly occupied by at least a portion of an intervertebral disc. The intervertebral disc is partially or completely removed prior to insertion of the prosthetic implant between the vertebrae. In another embodiment, the prosthetic implant is designed to be readily inserted by established surgical procedures, with minimal chances of surgical difficulty. In yet another embodiment, the geometry of the prosthetic implant ensures proper load bearing, desired load bearing and support through the vertebrae so as to reduce or minimize the likelihood of the prosthetic implant dislocating relative to the vertebrae either during surgery or during the post operative fusing process. In still another embodiment, the prosthetic implant includes a generally spherical or ellipsoidal body. The maximum radii of the generally spherical or ellipsoidal body can be varied depending upon the location of the prosthetic implant in the vertebrae. Typically, the maximum radii of the generally spherical or ellipsoidal body will vary from about 3–15 mm; however, other radii can be used. In one aspect of this embodiment, the maximum radii of the generally spherical or ellipsoidal body is selected so that the generally spherical or ellipsoidal body can be at least partially positioned between the two adjacently positioned vertebrae and the surrounding fibers and muscle that complete the spinal structure. In one particular aspect, the maximum radii of the generally spherical or ellipsoidal body is selected to cause two adjacently positioned vertebrae to at least partially separate from one another a distance greater than their relative positions prior to surgery. The spreading of the adjacently positioned vertebrae from their original positions results in the elastic nature of the surrounding tissue and muscles maintaining the inserted prosthetic implant in compression between the vertebrae. In another particular aspect, the maximum radii of the generally spherical or ellipsoidal body is selected to cause two adjacently positioned vertebrae to at least partially separate from one another a distance generally equal to or less than their relative positions prior to surgery. In still yet another embodiment, the prosthetic implant is capable of achieving arthrodesis (fusion) and/or arthroplasty (joint formation) between adjacent vertebrae, depending on the desired procedure. As such, the prosthetic implant allows the surgeon to cause either a multidirectional joint or a fusion to form between two of more vertebrae. In still another embodiment, the prosthetic implant reduces or eliminates nerve pressure caused by a damaged or removed disc.

In accordance with another aspect of the present invention, there is provided a prosthetic implant which includes a generally spherical or ellipsoidal body design to be inserted in a cavity between two adjacent vertebrae. In one embodiment, the prosthetic implant is substantially spherical. In another embodiment, the prosthetic implant is ellipsoidal. In still another embodiment, the prosthetic implant is made of a material that is inert or biologically compatible with the vertebrae and/or surrounding tissue about the vertebrae. The material of the prosthetic implant includes, but is not limited to, bone, stainless steel, titanium, chromemolybdenum, cobalt chromium alloy, ceramic (zirconium oxide ceramic, aluminum oxide ceramic, etc.), chrome or chrome alloys, cobalt or cobalt alloys, polycarbonate, polypropylene, polyethylene, polymethylmethacrylate, polysolfone types filled with glass and/or carbon fibers, and various types of carbon and fiber reinforced polymers. In one aspect of this embodiment, the material is wear resistant. In another aspect of this embodiment, the material has an increased frictional coefficient. In still another aspect of this embodiment, the material has a reduced frictional coefficient. In accordance with another embodiment, the prosthetic implant is designed to maintain a tension load of about ten to forty pounds, and more preferably about fifteen to thirty-five pounds on the disc tissue and/or vertebral endplate. This tension load facilitates in maintaining the prosthetic implant in position between the vertebrae and accelerates bone ingrowth between the vertebrae, if such bone growth is desired. In still another embodiment, the prosthetic implant is made of a material which closely approximates the elasticity of the vertebrae. In still yet another embodiment, the prosthetic implant is coated with, made up of, and/or contains a material which is radiolucent to enhance the visibility of the implant when exposed to X-rays. In a further embodiment, the prosthetic implant is coated with, made up of, and/or contains a material to enhance the visibility of the implant when exposed to sound waves, light waves, magnetic waves, and/or various types of electromagnetic waves.

In accordance with still another aspect of the present invention, the generally spherical or ellipsoidal body of the prosthetic implant includes a substantially smooth outer surface or includes regions having a substantially smooth outer surface to prevent or substantially prevent bone growth and/or other tissue growth on the substantially smooth surface and/or into the interior of the generally spherical or ellipsoidal body of the prosthetic implant. The substantially smooth surface of the generally spherical or ellipsoidal body allows the generally spherical or ellipsoidal body to move freely or relatively freely between two vertebrae. The growth of bone or other tissue into the generally spherical or ellipsoidal body can result in the generally spherical or ellipsoidal body becoming seized or at least partially retained in a position relative to one or both vertebrae. In one embodiment, the outer smooth surface material of the generally spherical or ellipsoidal body includes a wear resistant, relatively smooth material. The material may also have low frictional characteristics to allow for better movement between one or more vertebrae. In another embodiment, the substantially smooth surface has a total surface area that represents at least the majority of the total surface area of the generally spherical or ellipsoidal body. In one aspect of this embodiment, the substantially smooth surface has a total surface area that represents at least about 60 percent of the total surface area of the generally spherical or ellipsoidal body. In another aspect of this embodiment, the substantially smooth surface has a total surface area that represents at least about 70 percent of the total surface area of the generally spherical or ellipsoidal body. In yet another aspect of this embodiment, the substantially smooth surface has a total surface area that represents at least about 80 percent of the total surface area of the generally spherical or ellipsoidal body. In still another aspect of this embodiment, the substantially smooth surface has a total surface area that represents at least about 90 percent of the total surface area of the generally spherical or ellipsoidal body. In still yet another aspect of this embodiment, the substantially smooth surface has a total surface area that represents at least about 95 percent of the total surface area of the generally spherical or ellipsoidal body. In still another embodiment, the generally spherical or ellipsoidal body is at least partially coated with a material that reduces or eliminates voids and/or non-smooth surfaces in the outer surface of the generally spherical or ellipsoidal body. In one aspect of this embodiment, the coating is a biocompatible material. Non-limiting materials that can be used include polytetrafluoroethylene, or polymers and/or co-polymers that includes polytetrafluoroethylene. In another embodiment, the coated material can be applied to the generally spherical or ellipsoidal body by adhesive bonding, welding, soldering, shrink wrapping, melting, spray coating, hot dipping, electroplating, immersion coating, brush coating, and/or the like. The coated material can be biologically neutral or include one or more substances that inhibit bone and/or other tissue growth. In one aspect of this embodiment, the coating includes one or more substances that migrate from the coated material into the surrounding tissue. In one specific design, the one or more substances are inserted in, entrapped in and/or at least partially bonded to the coated material so as to at least partially control the time of release and/or release rate of the one or more substances into the surrounding tissue. In another embodiment, the coating material enhances the strength and/or durability of the prosthetic implant and/or hardens or softens the surface of the prosthetic implant.

In accordance with yet another aspect of the present invention, the generally spherical or ellipsoidal body of the prosthetic implant includes one or more smooth surfaces to promote bone growth and/or other tissue growth into the surface of the generally spherical or ellipsoidal body of the prosthetic implant. The one or more smooth surfaces allow for one or more surfaces of the generally spherical or ellipsoidal body to become partially or fully fused with one or more vertebrae. The smooth surface can be designed to be adapted to engage and/or anchor the underside surface of a vertebrae within the intervertebral disc space. In one embodiment, at least a portion of the surface of the generally spherical or ellipsoidal body is coated with a material that forms a smooth surface. The coated material can be biologically neutral or can include one or more substances that inhibit and/or promote bone or other tissue growth. In still another aspect of the embodiment, the coated material includes, but is not limited to, a natural and/or synthetic bone cement; polymer, co-polymer and/or urethane foam; autologous growth compound, powdered bone, bone and/or other tissue growth stimulating substances, bone, polyglycolate polymers or analogues, lactides, polydioxamone, polyglycolate, lactide/glycolide copolymers, and/or other tissue growth inhibiting substances and/or medicines. In another embodiment, the coated material can be applied to the generally spherical or ellipsoidal body by adhesive bonding, welding, soldering, shrink wrapping, melting, spray coating, hot dipping, electroplating, immersion coating, brush coating, and/or the like. The coated material can be biologically neutral or include one or more substances that inhibit bone and/or other tissue growth. In one aspect of this embodiment, the coating includes one or more substances that migrate from the coated material into the surrounding tissue. In one specific design, the one or more substances are inserted in, entrapped in and/or at least partially bonded to the coated material so as to at least partially control the time of release and/or release rate of the one or more substances into the surrounding tissue. In another embodiment, the coating material enhances the strength and/or durability of the prosthetic implant and/or hardens or softens the surface of the prosthetic implant.

In accordance with still another aspect of the present invention, the generally spherical or ellipsoidal body of the prosthetic implant includes one or more non-smooth surfaces and/or openings into the generally spherical or ellipsoidal body to promote bone growth and/or other tissue growth into the surface and/or interior of the generally spherical or ellipsoidal body of the prosthetic implant. The one or more non-smooth surfaces and/or openings in the generally spherical or ellipsoidal body allow one or more surfaces of the generally spherical or ellipsoidal body to become partially or fully fused with one or more vertebrae. The non-smooth surface can be designed to be adapted to engage with and/or anchor to the underside surface of a vertebrae within the intervertebral disc space. In one embodiment, the non-smooth surfaces include, but are not limited to, ridges, grooves, pits, holes, notches, slits, slots, channels, corrugations, and the like. In another embodiment, at least a portion of the surface of the generally spherical or ellipsoidal body is coated with a material that forms a non-smooth surface. The coated material is typically biocompatible. The coated material can be biologically neutral or include one or more substances that inhibit or promote bone and/or other tissue growth. In still another aspect of the embodiment, the coated material includes, but is not limited to, a natural and/or synthetic bone cement, polymer, co-polymer and/or urethane foam, autologous growth compound, powdered bone, bone and/or other tissue growth stimulating substances, bone, polyglycolate polymers or analogues, lactides, polydioxamone, polyglycolate, lactide/glycolide copolymers, and/or other tissue growth inhibiting substances and/or medicines. In another embodiment, the coated material can be applied to the generally spherical or ellipsoidal body by adhesive bonding, welding, soldering, shrink wrapping, melting, spray coating, hot dipping, electroplating, immersion coating, brush coating, and/or the like. The coated material can be biologically neutral or include one or more substances that inhibit bone and/or other tissue growth. In one aspect of this embodiment, the coating includes one or more substances that migrate from the coated material into the surrounding tissue. In one specific design, the one or more substances are inserted in, entrapped in and/or at least partially bonded to the coated material so as to at least partially control the time of release and/or release rate of the one or more substances into the surrounding tissue. In another embodiment, the coating material enhances the strength and/or durability of the prosthetic implant and/or hardens or softens the surface of the prosthetic implant.

In accordance with yet another aspect of the present invention, the generally spherical or ellipsoidal body includes one or more internal cavities. These cavities can include one or more passageways to the outer surface of the generally spherical or ellipsoidal body, or be at least partially isolated from the outer surface of the generally spherical or ellipsoidal body. In one embodiment, at least one of the cavities is substantially vacant. In another embodiment, at least one of the cavities includes one or more substances that promote the effectiveness of the prosthetic implant between at least two vertebrae. In one aspect of this embodiment, at least one of the substances include, but is not limited to, a substance which facilitates in the formation of a graft between one or more vertebrae. Such substance can include, but is not limited to, medicine, human tissue, animal tissue, synthetic tissue, human cells, animal cells, synthetic cells, and the like. In another aspect of this embodiment, at least one of the substances include, but is not limited to, a chemical compound that promotes bone or other tissue growth which inhibits rejection of the prosthetic implant, reduces infection, reduces inflammation, reduces pain, promotes healing of surrounding tissue, functions as a location and/or visual indicator, and/or the like. In still another aspect of this embodiment, one or more cavities are filled with bone material or a synthetic material, with or without a bone activating matter, such as hydroxyapatite bone or proteins, bone growth factor, or cartilage activation factor. In still yet another embodiment, one or more of the cavities in the outer surface of the generally spherical or ellipsoidal body allows blood supply and/or other body fluids to flow into and/or out of one or more of the cavities. In a further embodiment, the size or the passageway and/or opening to the outer surface of the generally spherical or ellipsoidal body can be selected to control the amount and/or rate of the one or more substances in the one or more cavities that exits the cavities. In yet a further embodiment, the size or the passageway and/or opening to the outer surface of the generally spherical or ellipsoidal body can be selected to control the amount and/or rate of bone and/or other tissue growth that occurs in the opening and/or passageway and into the one or more cavities. In still another embodiment, the substance in one or more cavities can be at least partially pre-packed in the cavity prior to inserting the prosthetic implant between one or more vertebrae, and/or the substance can be at least partially packed into one or more cavities after the prosthetic implant is inserted between one or more vertebrae. In still yet another embodiment, the volume of each of the one or more cavities in the generally spherical or ellipsoidal body is less than the total volume of the generally spherical or ellipsoidal body. In one aspect of this embodiment, the volume of each of the one or more cavities in the generally spherical or ellipsoidal body is less than about 50% of the total volume of the generally spherical or ellipsoidal body. The volume of two or more cavities can be the same or different. In another aspect of this embodiment, the volume of each of the one or more cavities in the generally spherical or ellipsoidal body is less than about 40% of the total volume of the generally spherical or ellipsoidal body. In still another aspect of this embodiment, the volume of each of the one or more cavities in the generally spherical or ellipsoidal body is less than about 30% of the total volume of the generally spherical or ellipsoidal body. In yet another aspect of this embodiment, the volume of each of the one or more cavities in the generally spherical or ellipsoidal body is less than about 20% of the total volume of the generally spherical or ellipsoidal body. In still yet another aspect of this embodiment, the volume of each of the one or more cavities in the generally spherical or ellipsoidal body is less than about 10% of the total volume of the generally spherical or ellipsoidal body. In still yet another embodiment, the sum of the volumes of the one or more cavities in the generally spherical or ellipsoidal body is less than the total volume of the generally spherical or ellipsoidal body. In one aspect of this embodiment, the sum of the volumes of the one or more cavities in the generally spherical or ellipsoidal body is less than about 50% of the total volume of the generally spherical or ellipsoidal body. In another aspect of this embodiment, the sum of the volumes of the one or more cavities in the generally spherical or ellipsoidal body is less than about 40% of the total volume of the generally spherical or ellipsoidal body. In still another aspect of this embodiment, the sum of the volumes of the one or more cavities in the generally spherical or ellipsoidal body is less than about 30% of the total volume of the generally spherical or ellipsoidal body. In yet another aspect of this embodiment, the sum of the volumes of the one or more cavities in the generally spherical or ellipsoidal body is less than about 20% of the total volume of the generally spherical or ellipsoidal body. In still yet another aspect of this embodiment, the sum of the volumes of the one or more cavities in the generally spherical or ellipsoidal body is less than about 10% of the total volume of the generally spherical or ellipsoidal body. In yet another embodiment of the invention, at least two of the cavities in the generally spherical or ellipsoidal body intersect one another. In one aspect of this embodiment, two or more cavities intersect one another at substantially the center of the generally spherical or ellipsoidal body. In another aspect of this embodiment, two or more cavities intersect one another generally off center of the generally spherical or ellipsoidal body. In still yet another embodiment of the invention, at least one of the cavities in the generally spherical or ellipsoidal body at least partially includes a generally cylindrical portion. In one aspect of this embodiment, at least one of the cavities in the generally spherical or ellipsoidal body is substantially cylindrical.

In accordance with still yet another aspect of the present invention, the generally spherical or ellipsoidal body of the prosthetic implant includes one or more openings in the outer wall of the generally spherical or ellipsoidal body of the prosthetic implant to facilitate in the positioning of the prosthetic implant between the vertebrae and/or to secure the prosthetic implant in place within the intervertebral disc space. In one embodiment, one or more of the openings in the outer wall of the generally spherical or ellipsoidal body is adapted to receive an instrument for guiding and/or inserting the prosthetic implant between the vertebrae of the spine by an anterior, posterior, lateral, and/or latroscopic approach into the spinal column. The one or more openings allow a surgeon to select the best approach for inserting the prosthetic implant in the intervertebral disc space. In one aspect of this embodiment, the instrument opening includes a securing mechanism such as, but not limited to, a thread, in the opening to secure the instrument within the opening.

In accordance with still yet another aspect of the present invention, the generally spherical or ellipsoidal body of the prosthetic implant includes one or more openings in the outer wall of the generally spherical or ellipsoidal body of the prosthetic implant that can be at least partially closed prior to, during and/or after the prosthetic implant is inserted between one or more vertebrae. In one embodiment, a cap is used to at least partially close one or more openings in the generally spherical or ellipsoidal body. In one aspect of this embodiment, the cap substantially seals one or more openings. In another aspect of this embodiment, the cap alters the size of the one or more openings. The altered size of the one or more openings can be used to control the amount and/or rate of substances exiting the one or more openings and/or to control the rate and/or amount of substances, bone and/or other tissue entering the opening. In another aspect of this embodiment, the cap can be made of a porous material or a non-porous material. In another embodiment, the cap is adapted to receive an instrument for guiding and/or inserting the cap into one or more openings in the generally spherical or ellipsoidal body. In still another embodiment, the cap is made of a biocompatible material. In one aspect of this embodiment, the cap is made or includes a material that is the same as the material make-up of the generally spherical or ellipsoidal body. In another aspect of this embodiment, the cap is made of or includes a material that is different from the material of the generally spherical or ellipsoidal body. In yet another embodiment, the cap is made of a material that fuses with the surrounding bone and/or tissue while the prosthetic implant is between one or more vertebrae. In yet another embodiment, the cap is made of a material that resists fusion with the surrounding bone and/or tissue while the prosthetic implant is between one or more vertebrae. In still yet another embodiment, the cap is made of a material that decomposes after the prosthetic implant is positioned between one or more vertebrae.

In accordance with another aspect of the present invention, at least one or more surfaces of the prosthetic implant are rounded off so as not to be sharp. Rounding off the surfaces reduces and/or eliminates pinching of the nerve leading from the spinal cord which can result in pain, damage and/or paralysis to the individual. The rounded surfaces avoid or minimize nerve pressure that can be exerted on the nerves intervertebrally exiting the spinal cord. The one or more rounded off surfaces also facilitate with the insertion of the prosthetic implant within the intervertebral disc space. In one embodiment, substantially all the surfaces of the prosthetic implant are rounded off.

In accordance with still another aspect of the present invention, the prosthetic implant includes at least one stabilizer positioned at least partially about the outer surface of the generally spherical or ellipsoidal body of the prosthetic implant. The stabilizer is designed to facilitate in at least partially orienting the prosthetic implant between one or more vertebrae, limiting the amount of movement of the generally spherical or ellipsoidal body between one or more vertebrae and/or facilitating in the insertion of the prosthetic implant between one or more vertebrae. In one embodiment, at least one stabilizer is positioned substantially about the generally spherical or ellipsoidal body. In one aspect of this embodiment, at least one stabilizer is positioned substantially about the central axis of the generally spherical or ellipsoidal body. In another aspect of this embodiment, at least one stabilizer is positioned substantially off-center of the central axis of the generally spherical or ellipsoidal body. In another embodiment, the stabilizer is substantially disc shaped; however, the shape of the stabilizer is in no way limited to such a shape. In yet another embodiment, the stabilizer includes one or more tapered edges. In still another embodiment, the stabilizer is at least partially made of a porous material, a non-porous material, a non-biodegradable material, and/or a biodegradable material. In still yet another embodiment, the stabilizer can be coated with, contain and/or be made of a substance that promotes bone and/or other tissue growth, to inhibit rejection of the prosthetic implant, reduce infection, reduce inflammation, reduce pain, promote healing of surrounding tissue, function as a location and/or visual indicator, and/or the like. In one aspect of this embodiment, the stabilizer includes, but is not limited to, a substance that includes medicine, human tissue, animal tissue, synthetic tissue, human cells, animal cells, synthetic cells, and/or bone activating matter. In another aspect of this embodiment, the stabilizer includes, but is not limited to, a substance that includes bone, stainless steel, titanium, chromemolybdenum, cobalt chromium alloy, ceramic (zirconium oxide ceramic, aluminum oxide ceramic, etc.), chrome or chrome alloys, cobalt or cobalt alloys, polycarbonate, polypropylene, polyethylene, polymethylmethacrylate, polysolfone types filled with glass and/or carbon fibers, and various types of carbon and fiber reinforced polymers. In one aspect of this embodiment, the material is wear resistant. In another aspect of this embodiment, the material has an increased frictional coefficient. In still another aspect of this embodiment, the material has a reduced frictional coefficient. In still another aspect of this embodiment, the stabilizer and/or coating that is at least partially coated can be made of a material that results in smooth surfaces, rough surfaces, low frictional surfaces, wear resistant surfaces, and/or the like. In another embodiment, the stabilizer can include one or more openings and/or cavities. The openings and/or cavities can include various types of substances to promote bone and/or other tissue growth, inhibit rejection of the prosthetic implant, reduce infection, reduce inflammation, reduce pain, promote healing of surrounding tissue, function as a location and/or visual indicator, and/or the like. In still another embodiment, the stabilizer includes a coating with one or more substances that migrate from the coated material into the surrounding tissue. In one specific design, the one or more substances are inserted in, entrapped in and/or at least partially bonded to the coated material so as to at least partially control the time of release and/or release rate of the one or more substances into the surrounding tissue. In another embodiment, the coating material enhances the strength and/or durability of the prosthetic implant and/or hardens or softens the surface of the stabilizer. In a further embodiment, the stabilizer can be detached from, or is substantially permanently connected to, the generally spherical or ellipsoidal body of the prosthetic implant. In one aspect of this embodiment, the stabilizer and the generally spherical or ellipsoidal body constitute a single component. In still yet a further embodiment, the maximum radial width of the stabilizer is less than about three times the maximum radius of the generally spherical or ellipsoidal body of the prosthetic implant. In one aspect of this embodiment, the maximum radial width of the stabilizer is no more than about two times the maximum radius of the generally spherical or ellipsoidal body of the prosthetic implant. In another embodiment, the angle of articulation of the stabilizer in relation to the outer surface of the generally spherical or ellipsoidal body can be constant or vary from an angle of less than about 0.01° to about 180°. In still another embodiment, the maximum thickness of the stabilizer is generally less than or equal to the maximum diameter of the generally spherical or ellipsoidal body. In one aspect of this embodiment, the maximum thickness of the stabilizer is less than the maximum diameter of the generally spherical or ellipsoidal body. In another aspect of this embodiment, the maximum thickness of the stabilizer at least closely adjacent to the generally spherical or ellipsoidal body is greater than or equal to the maximum thickness of the stabilizer at the outer edge of the stabilizer. In one particular design, the width of the stabilizer reduces from a point at least closely adjacent to the generally spherical or ellipsoidal body to the outer edge of the stabilizer. In a specific design, the taper is generally constant.

It is an object of the present invention to provide an improved prosthetic implant for insertion between two vertebrae.

It is another and/or alternative object of the present invention to provide a prosthetic implant which at least partially emulates the space between the vertebrae.

Yet another and/or alternative object of the present invention is to provide a prosthetic implant which includes one or more non-smooth surfaces to help secure the prosthetic implant in position between the vertebrae.

It is still yet another and/or alternative object of the present invention to provide a prosthetic implant which provides improved spinal support fixation and methodology which provides stability between adjacent vertebrae and in which the shape will facilitate in securing the prosthetic implant between the vertebrae.

A further and/or alternative object of the present invention is to provide a prosthetic implant that includes a generally spherical or ellipsoidal body.

Still a further and/or alternative object of the present invention is to provide a prosthetic implant that includes a stabilizer.

Yet a further and/or alternative object of the present invention is to provide a prosthetic implant that includes one or more smooth surfaces to inhibit bone and/or other tissue growth on the smooth surface.

Still yet another and/or alternative object of the present invention is to provide a prosthetic implant that includes a cap to at least partially alter the size of an opening in the outer surface of the prosthetic implant.

Another and/or alternative object of the present invention is to provide an apparatus which will at least partially aid in the positioning of the prosthetic implant between the vertebrae.

Still yet another and/or alternative object of the present invention is to provide a prosthetic implant which has one or more openings that can receive packing material to facilitate in the fusion of two adjacently positioned vertebrae and/or the healing process after insertion of the prosthetic implant.

A further and/or alternative object of the present invention is to provide a prosthetic implant which can be easily and efficiently positioned between two vertebrae and which reduces the failure rate of prosthetic implants between the vertebrae.

It is still another and/or alternative object of the present invention to provide a prosthetic implant which includes one or more surfaces that reduce pinching with the spinal cord and other body parts closely adjacent to the prosthetic implant.

It is another and/or alternative object of the present invention to provide a prosthetic implant that is at least partially made of a biologically compatible material.

It is another and/or alternative object of the present invention to provide a prosthetic implant that is at least partially made of and/or includes a material that enhances the visibility of the implant when exposed to X-rays, sound waves, light waves, magnetic waves, and/or various other types of electromagnetic waves.

It is another and/or alternative object of the present invention to provide a prosthetic implant that is at least partially made of a material which closely approximates the elasticity of the vertebrae and/or the intervertebral disc.

These and other objects of the invention will become apparent to those skilled in the art upon reading and understanding the following detailed description of preferred embodiments taken together with the drawings.

BRIEF DESCRIPTION OF THE DRAWINGS

The invention may take physical form in certain parts and arrangement of parts, preferred embodiments of which will be described in detail and illustrated in the accompanying drawings which form a part hereof and wherein.

DESCRIPTION OF THE PREFERRED EMBODIMENTS

Referring to the drawings, wherein the showings are for the purpose of illustrating the preferred embodiment of the invention only and not for the purpose of limiting same, FIGS. 1, and 3–8 illustrate a prosthetic device or implant 10 which is designed to be inserted in an intervertebral disc space between two vertebrae of the spinal column. Prosthetic implant 10 is illustrated as having a spherical body 20 that has an outer surface 22. spherical body 20 can be made of a variety of materials such as, but not limited to, bone, stainless steel, titanium, chromemolybdenum, cobalt chromium alloy, ceramic (zirconium oxide ceramic, aluminum oxide ceramic, etc.), chrome or chrome alloys, cobalt or cobalt alloys, polycarbonate, polypropylene, polyethylene, polymethylmethacrylate, polysolfone types filled with glass and/or carbon fibers, and various types of carbon and fiber reinforced polymers. The particular material or materials selected will generally depend on the location of the implant and the various objectives to be accomplished by the implant. Additionally, spherical body 20 can include medicine, bone and/or tissue growth promoters, bone and/or tissue growth inhibitors, etc. that are mixed with the materials of spherical body 20 which are designed to flow or otherwise escape from spherical body 20 and enter the bone, tissue and/or fluids about the implant, and/or interact with the bone, tissue and/or fluids about the implant.

Figure 1:
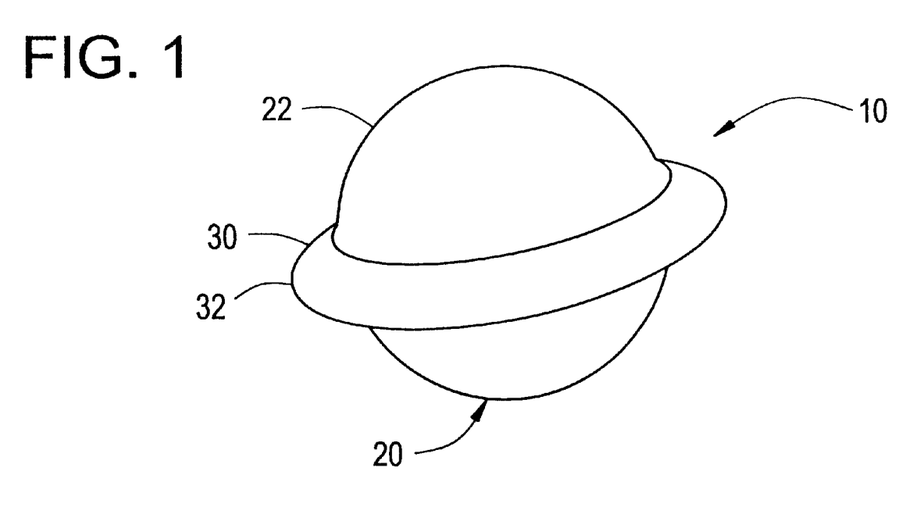
FIG. 1 is an enlarged perspective view of the prosthetic implant of the present invention.

Referring now to FIG. 1, implant 10 includes a spherical body 20 that has an outer surface 22 which is substantially smooth. The interior of spherical body 20 can be solid, hollow or have one or more cavities. If spherical body 20 includes one or more cavities, the cavities can be empty or at least partially filled with a material which alters the physical characteristics of spherical body 20 (i.e. weight distribution, density distribution, etc.) and/or which is designed to flow or otherwise escape the void and enter the bone, tissue and/or fluids about the implant (i.e. medicine, bone and/or tissue growth promoters, bone and/or tissue growth inhibitors, etc.). Implant 10 also includes a stabilizer 30 connected to spherical body 20. Stabilizer 30 is disc shaped and extends about the central axis of spherical body 20. Stabilizer 30 and spherical body 20 are shown to be formed of a single piece of material. Generally, the stabilizer is made of a similar material as spherical body 20; however, the stabilizer can include different or additional materials. As can be appreciated, stabilizer 30 can be a separate component that is later connected to outer surface 22. Stabilizer 30 is designed to facilitate in at least partially orienting the prosthetic implant between one or more vertebrae, limiting the amount of movement of the generally spherical or ellipsoidal body between one or more vertebrae, and/or facilitating in the insertion of the prosthetic implant between one or more vertebrae. Edge 32 of stabilizer 30 is a rounded, non-sharp edge. The rounding off of the surfaces of the stabilizer reduces and/or eliminates pinching of the nerve leading from the spinal cord which can result in pain, damage and/or paralysis to the individual. Stabilizer 30 also has a thickness that reduces as the distance increases from spherical body 20. Stabilizer 30 also has a maximum thickness that is less than the diameter of spherical body 20. Generally, the maximum thickness of the stabilizer is less than about 1.5 times the diameter of spherical body 20, and typically less than about 4 times the diameter of spherical body 20. Stabilizer 30 is shown to have a generally constant width that radially extends outwardly from spherical body 20; however, the width of the stabilizer can vary. Generally, the maximum width of the stabilizer is less than about 2 times the diameter of spherical body 20, and typically less than about 1 times the diameter of spherical body 20.

Figure 2:
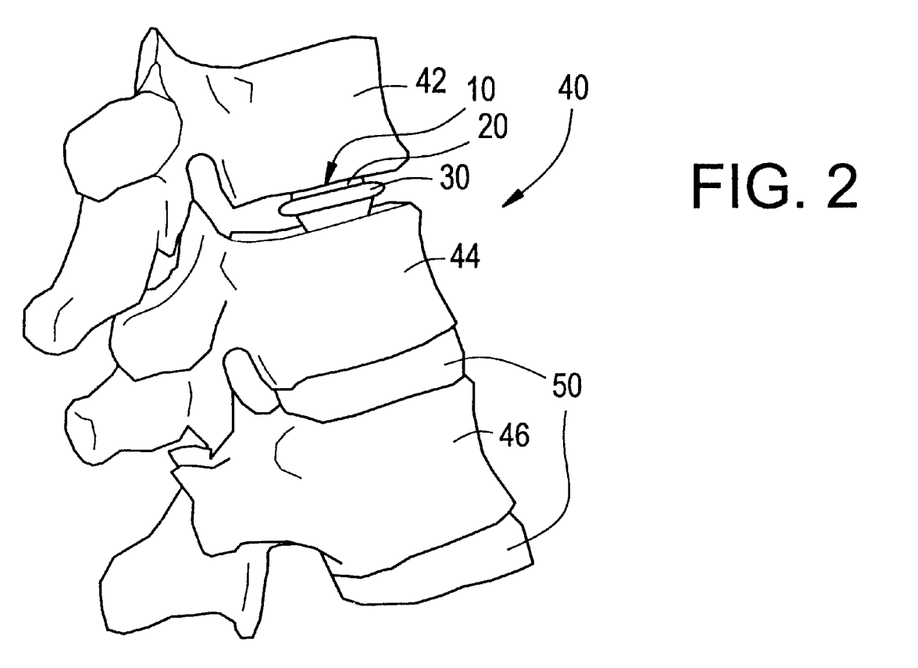
FIG. 2 is an enlarged side elevation view of a portion of a spinal column which includes the prosthetic implant of the present invention positioned between two adjacently positioned vertebrae.

Referring now to FIG. 2, implant 10 is shown as being inserted into a human vertebrae column 40. Human vertebrae column 40 includes several vertebrae 42, 44, 46 and includes intervertebral disc 50 positioned between two adjacently positioned vertebrae. Implant 10 is designed to partially or fully replace a damaged intervertebral disc. As shown in FIG. 2, vertebrae 42 and 44 are separated by, and at least partially supported on, spherical body 20 of prosthetic implant 10. The remaining vertebrae are illustrated as being supported on, and separated by, intervertebral disc 50 which maintains a space between the adjoining vertebrae. The damaged portions of intervertebral disc 50 have been removed from the region between vertebrae 42 and 44 prior to prosthetic implant 10 being inserted therebetween. The inner surfaces of vertebrae 42 and 44 are also prepared prior to implant 10 being inserted therebetween. Such preparation typically includes cleaning the region between the vertebrae of unwanted materials, removing bone and/or tissue from the surface of one or more vertebrae, inserting separators between the vertebrae, and the like. After the region between the vertebrae has been prepared, implant 10 is inserted into the space between the vertebrae. Depending of the design of implant 10, the prosthetic implant will achieve arthrodesis (fusion) and/or arthroplasty (joint formation) between adjacent vertebrae. Once implant 10 has been inserted between vertebrae 42 and 44, stabilizer 30 limits the movement of implant 10 between the vertebrae.

Figure 3:
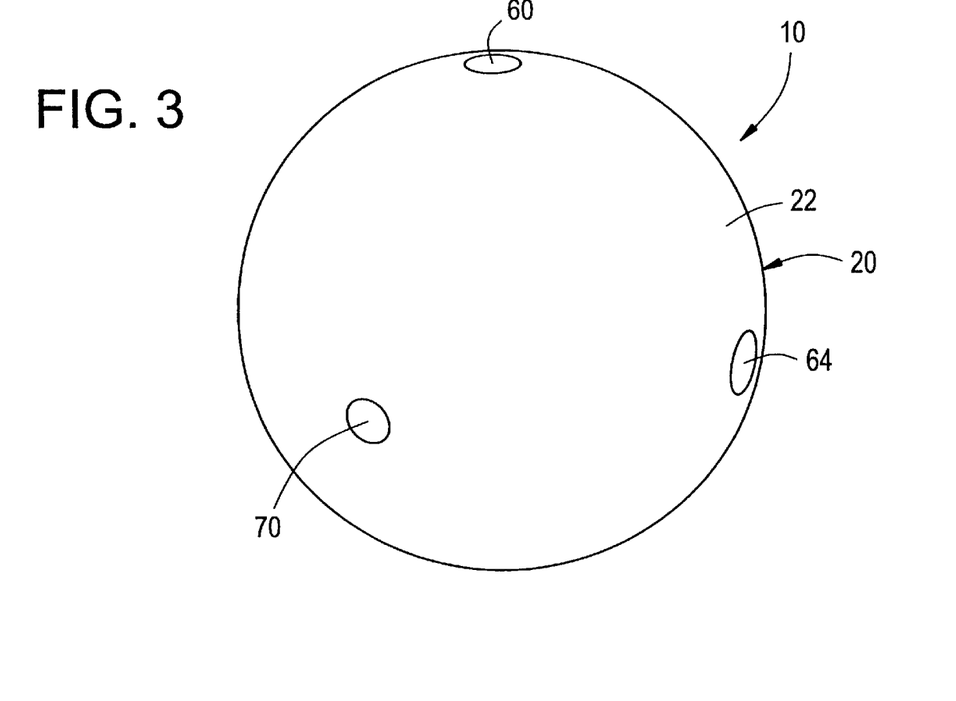
FIG. 3 is an enlarged perspective view of a modified prosthetic implant of the present invention.

Referring now to FIGS. 3–8, other designs of the prosthetic implant are illustrated. Referring specifically to FIG. 3, prosthetic implant 10 includes a spherical body 20 that has a substantially smooth outer surface 22. The interior of spherical body 20 can be solid, hollow or have one or more cavities. If spherical body 20 includes one or more cavities, the cavities can be empty or at least partially filled with a material which alters the physical characteristics of spherical body 20 (i.e. weight distribution, density distribution, etc.) and/or which is designed to flow or otherwise escape the void and enter the bone, tissue and/or fluids about the implant (i.e. medicine, bone and/or tissue growth promoters, bone and/or tissue growth inhibitors, etc.). Implant 10 is also shown has not having a stabilizer. Spherical body 20 includes several openings 60, 64 and 70. The openings are illustrated as being circular shaped; however, other shapes can be used. The size of the openings is selected so that various materials can be pack therein and/or to enable bone and/or tissue to grow in the opening to facilitate in the fusion of the body to a vertebrae. When materials are packed into the openings, the packed material typically includes, but is not limited to, medicine, tissue, cells, and the like. One or more of the openings can also be used to enable an instrument to be connected to the implant to facilitate in the insertion and/or positioning of the implant between the vertebrae. The instrument can be used to insert the prosthetic implant in the intervertebral disc space in a number of different approaches such as from an anterior, posterior, lateral, and/or lateralscopic approach to the vertebrae. The opening for the instrument is typically threaded to receive a threaded instrument. The threaded opening allows an instrument to be simply secured to and/or removed from the prosthetic implant 10. The instrument opening can also be used to secure pedicle screws to the prosthetic implant to facilitate in the attachment of a rod or plate stabilization system to the prosthetic implant.

Figure 4:
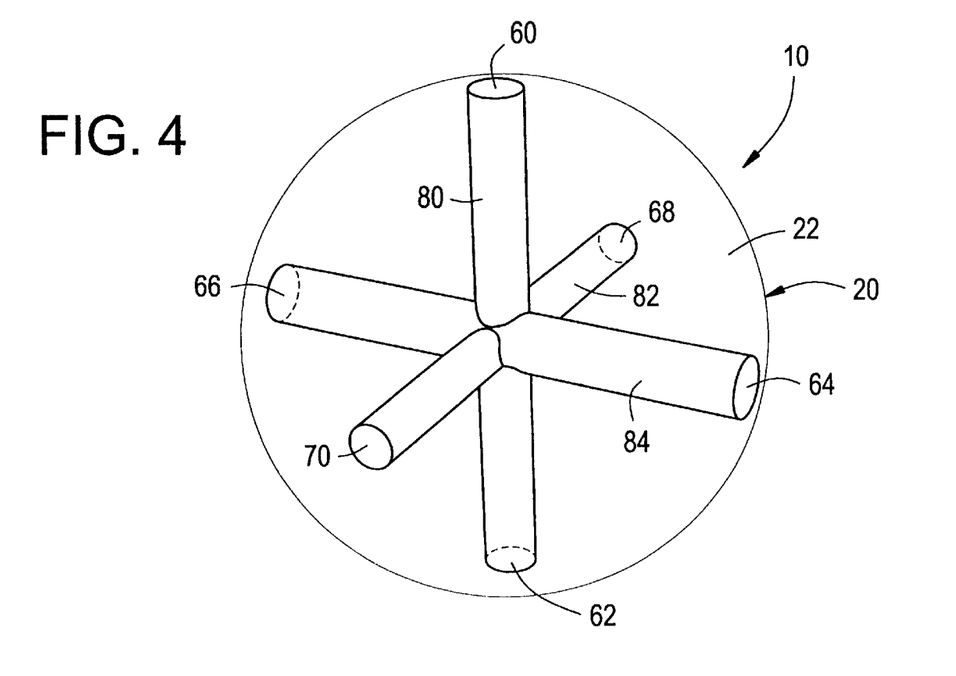
FIG. 4 is an enlarged perspective view of another modified prosthetic implant of the present invention.

Referring now to FIG. 4, prosthetic implant 10 includes a spherical body 20 that has a substantially smooth outer surface 22. Implant 10 is also shown has not having a stabilizer. Implant 10 also includes a plurality of cavities 80, 82 and 84. The cavities have a substantially cylindrical shape and extend through implant 10. The cavities are illustrated as all passing through the center of spherical body 20; however, it can be appreciated that one or more of the cavities do not pass through the center of spherical body 20. Cavity 80 includes openings 60 and 62, cavity 82 includes openings 68 and 70 and cavity 84 includes openings 64 and 66. The cavities typically include material packed therein; however, the cavities can be empty to allow fluids to flow therethrough. One or more of the openings can also be used to enable an instrument to be connected to the implant to facilitate in the insertion and/or positioning of the implant between the vertebrae. The remaining portion of the interior of spherical body 20 can be solid, hollow or have one or more cavities. If spherical body 20 includes one or more of these cavities, the cavities can be empty or at least partially filled with a material which alters the physical characteristics of spherical body 20 (i.e. weight distribution, density distribution, etc.) and/or which is designed to flow or otherwise escape the void and enter the bone, tissue and/or fluids about the implant (i.e. medicine, bone and/or tissue growth promoters, bone and/or tissue growth inhibitors, etc.).

Figure 5:
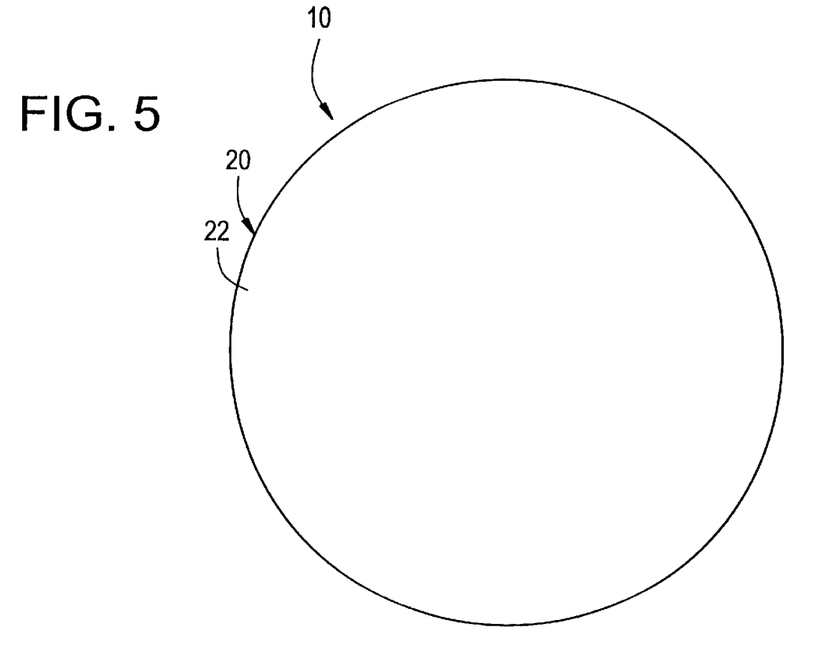
FIG. 5 is an enlarged perspective view of still another modified prosthetic implant of the present invention.

Referring now to FIG. 5, prosthetic implant 10 includes a spherical body 20 that has a substantially smooth outer surface 22. Implant 10 is also shown has not having a stabilizer. Implant 10 is further illustrated as not having any openings. The interior of spherical body 20 can be solid, hollow or have one or more cavities. If spherical body 20 includes one or more cavities, the cavities can be empty or at least partially filled with a material which alters the physical characteristics of spherical body 20 (i.e. weight distribution, density distribution, etc.) and/or which is designed to flow or otherwise escape the void and enter the bone, tissue and/or fluids about the implant (i.e. medicine, bone and/or tissue growth promoters, bone and/or tissue growth inhibitors, etc.).

Figure 6:
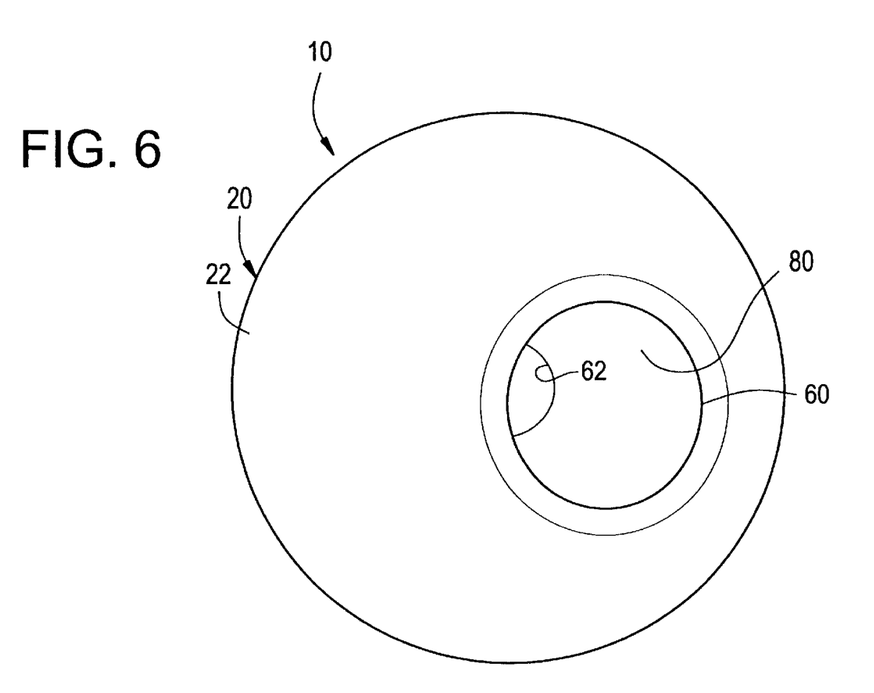
FIG. 6 is an enlarged perspective view of yet another modified prosthetic implant of the present invention.

Referring now to FIG. 6, prosthetic implant 10 includes a spherical body 20 that has a substantially smooth outer surface 22. Implant 10 is also shown has not having a stabilizer. Implant 10 is further illustrated as having two openings 60 and 62 and a cylindrical cavity 80 extending therebetween. The cavities typically include material packed therein; however, the cavities can be empty to allow fluids to flow therethrough. The single cavity is illustrated as having a volume that is greater than the individual volumes of cavities 80, 82 and 84 of FIG. 4. Typically the volume of cavity 80 of FIG. 6 is less than half the volume of spherical body 20. The remaining portion of the interior of spherical body 20 can be solid, hollow or have one or more cavities. If spherical body 20 includes one or more of these cavities, the cavities can be empty or at least partially filled with a material which alters the physical characteristics of spherical body 20 (i.e. weight distribution, density distribution, etc.) and/or which is designed to flow or otherwise escape the void and enter the bone, tissue and/or fluids about the implant (i.e. medicine, bone and/or tissue growth promoters, bone and/or tissue growth inhibitors, etc.).

Figure 7:
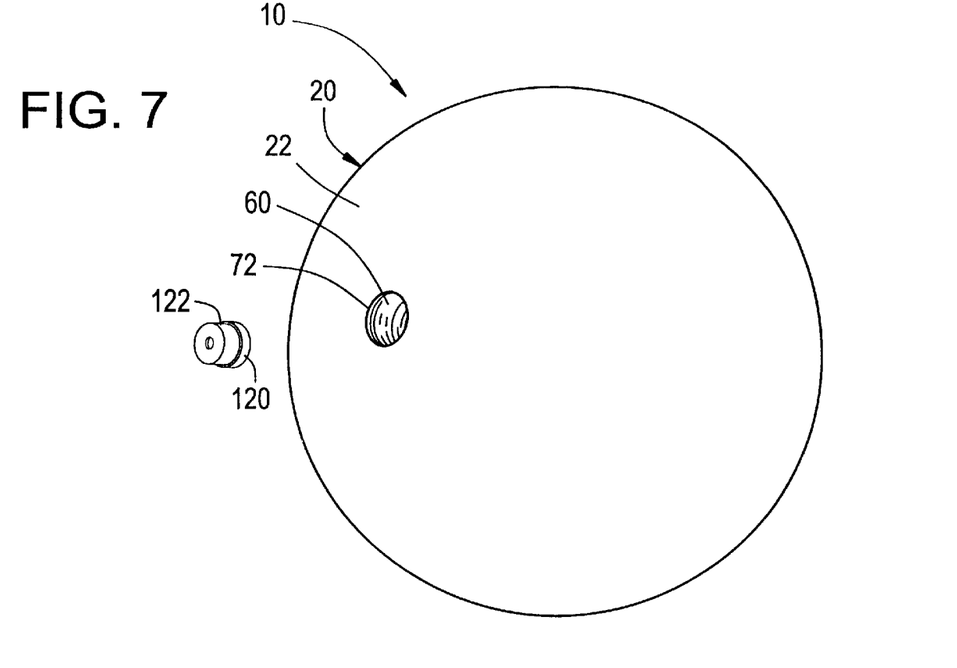
FIG. 7 is an enlarged perspective view of still yet another modified prosthetic implant of the present invention.

Referring now to FIG. 7, implant 10 is similar to the implant shown in FIG. 3, but includes a single opening 60. Opening 60 includes a threaded interior 72 that is designed to receive an instrument as described above and/or a cap 120. Cap 120 includes threading 122 that threads into opening 60 to at least partially close opening 60.

Figure 8:
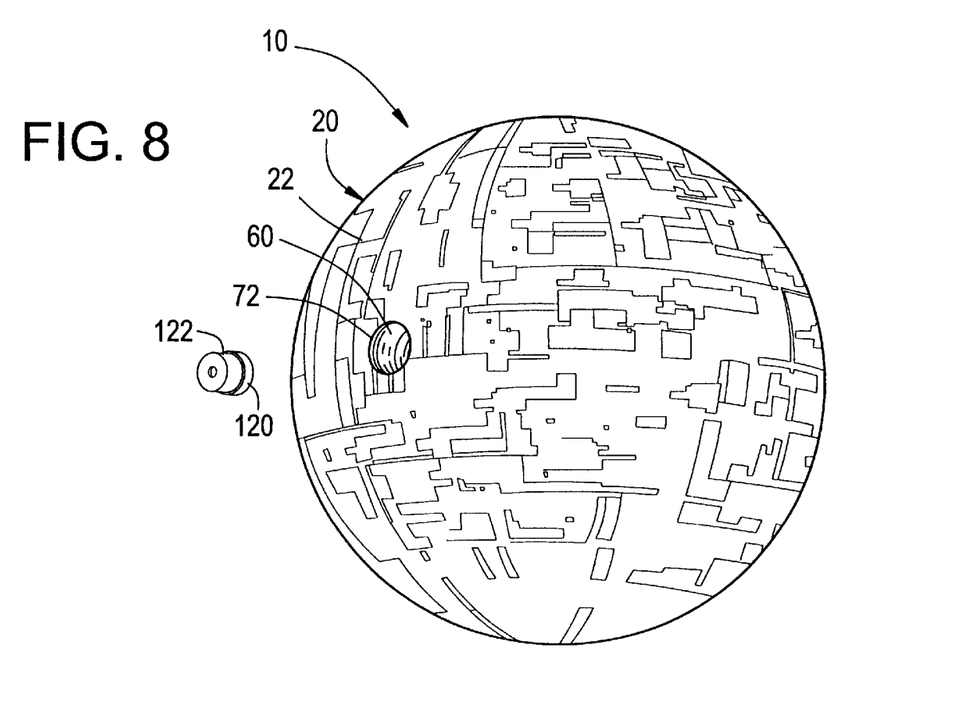
FIG. 8 is an enlarged perspective view of a further modified prosthetic implant of the present invention.

Referring now to FIG. 8, implant 10 is similar to the implant shown in FIG. 7, but outer surface 22 is a non-smooth surface. The non-smooth surface openings enable the implant to become partially or fully fused with one or more vertebrae. The non-smooth surface can also be designed to engage with and/or anchor to the underside surface of a vertebrae within the intervertebral disc space.

Figure 9:
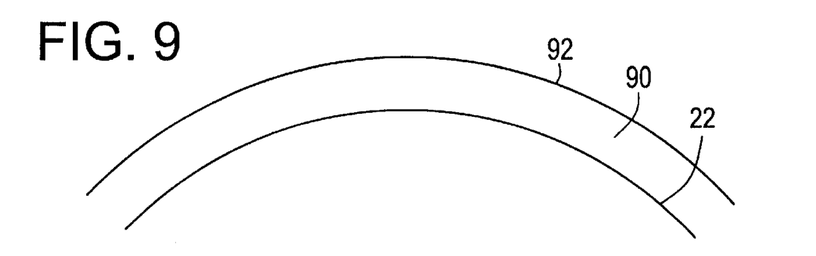
FIG. 9 is an enlarged sectional view of the surface of the prosthetic implant illustrating a coating material applied to a smooth outer surface of the body of the prosthetic implant.
Figure 10:
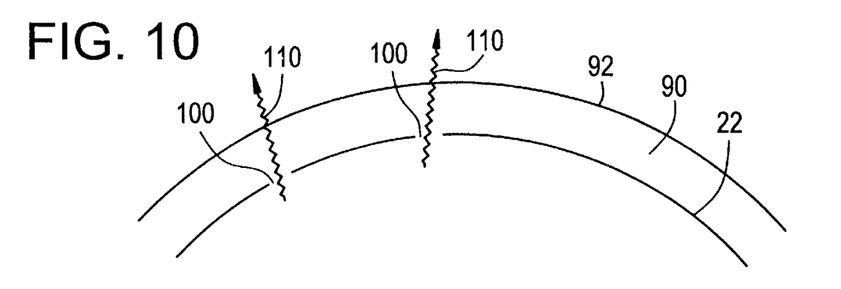
FIG. 10 is an enlarged sectional view of the surface of the prosthetic implant illustrating a coating material applied to an outer surface of the body of the prosthetic implant that has a plurality of openings.
Figure 11:
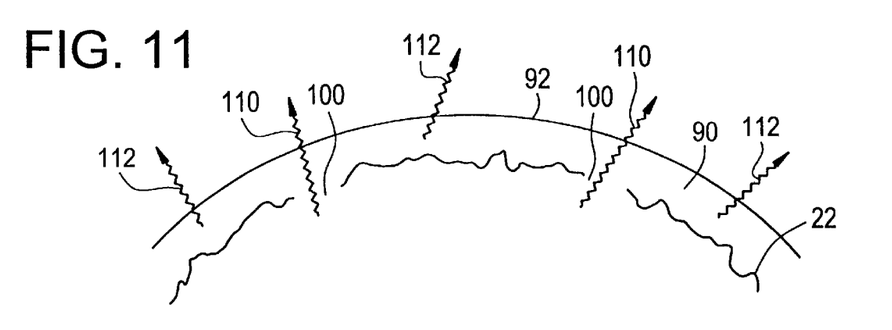
FIG. 11 is an enlarged sectional view of the surface of the prosthetic implant illustrating a coating material applied to a non-smooth outer surface of the body of the prosthetic implant that has a plurality of openings; and, FIG. 12 is an enlarged sectional view of the surface of the prosthetic implant illustrating a coating material having a non-smooth surface applied to the outer surface of the body of the prosthetic implant.
Figure 12:
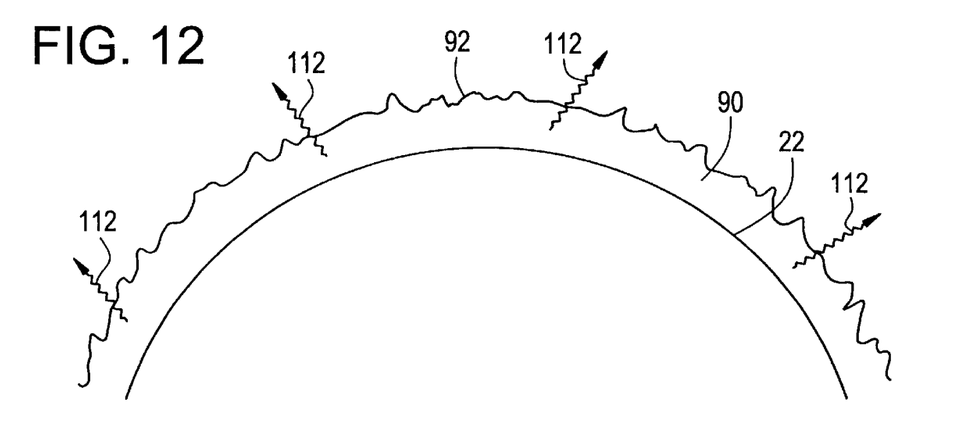

Referring now to FIGS. 9–12, an implant is shown to have an outer surface 22 that is at least partially coated with a coating 90. Coating 90 can form a substantially smooth outer surface 92 as shown in FIGS. 9–11 or have a non-smooth surface 92 as shown in FIG. 12. Coating 90 can be made of a variety of materials. Typically, coating 90 includes one or more materials that is different from the material composition of the outer surface 22 of spherical body 20. Coating 90 can also have a variety of functions such as, but not limited to, forming a substantially smooth and durable surface over a substantially smooth outer surface 22 of spherical body 20 as shown in FIG. 9, forming a substantially smooth and durable surface over a substantially smooth outer surface 22 of spherical body 20 and to at least partially cover openings 100 in the surface of spherical body 20 as shown in FIG. 10, forming a substantially smooth and durable surface of the prosthetic implant over a non-smooth outer surface 22 of spherical body 20 and to at least partially cover openings 100 in the surface of spherical body 20 as shown in FIG. 11, or forming a non-smooth surface over a substantially smooth outer surface 22 of spherical body 20 as shown in FIG. 12. As can be appreciated, coating 90 can be at least partially coated onto the stabilizer of the implant when the implant includes a stabilizer.

As shown in FIG. 10, a substance 110 flows from opening 100 and through coating 90. Coating 90 can be formulated to control the flow rate of substance 110 out of opening 100. The substance can be any number of materials that promote bone and/or other tissue growth, inhibit rejection of the prosthetic implant, reduce infection, reduce inflammation, reduce pain, promote healing of surrounding tissue, function as a location and/or visual indicator, and/or the like. Referring now to FIGS. 11 and 12, coating 90 includes a substance 112 that is released from the coating. This substance can be any number of materials that promote bone and/or other tissue growth, inhibit rejection of the prosthetic implant, reduce infection, reduce inflammation, reduce pain, promote healing of surrounding tissue, function as a location and/or visual indicator, and/or the like.

The invention has been described with reference to the preferred embodiments. These and other modifications of the preferred embodiments as well as other. embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

We claim:

1. A prosthetic implant to at least partially support adjoining vertebrae in a spinal column, comprising a prosthetic implant having a substantially spherical or ellipsoidal body that includes an exterior surface, said exterior surface including at least one non-growth outer surface that at least partially inhibits growth on at least one said non-growth outer surface while positioned between adjoining vertebrae, said substantially spherical or ellipsoidal body being formed of a material designed to maintain a tension load of at least about ten pounds without substantially deforming, less than about 50% of the volume of said substantially spherical or ellipsoidal body constituting one or more cavities.

2. The prosthetic implant as defined in claim 1, wherein said at least one non-growth outer surface having a surface area, said surface area being at least about 80 percent of a total outer surface area of said substantially spherical or ellipsoidal body.

3. The prosthetic implant as defined in claim 1, wherein said body includes at least one opening.

4. The prosthetic implant as defined in claim 3, wherein at least a portion of said non-growth outer surface is formed by a coating material applied to at least a portion of said exterior surface of said substantially spherical or ellipsoidal body.

5. The prosthetic implant as defined in claim 4, wherein said coating material at least partially covers at least one opening in said exterior surface of said substantially spherical or ellipsoidal body.

6. The prosthetic implant as defined in claim 5, wherein at least one opening includes a substance to at least partially inhibit tissue growth in said opening.

7. The prosthetic implant as defined in claim 6, wherein said coating material includes a substance to at least partially inhibit tissue growth on said coating material.

8. The prosthetic implant as defined in claim 7, including at least one stabilizer connected to and positioned at least partially about said exterior surface of said substantially spherical or ellipsoidal body, said at least one stabilizer at least partially limiting movement of said substantially spherical or ellipsoidal body between said adjoining vertebrae.

9. The prosthetic implant as defined in claim 8, wherein said at least one stabilizer includes a substance to at least partially inhibit tissue growth on said at least one stabilizer.

10. The prosthetic implant as defined in claim 9, including an instrument cavity adapted to receive an instrument to guide said prosthetic implant between adjoining vertebrae in a spinal column, to receive an implant to secure said prosthetic implant in position relative to said vertebrae, and combinations thereof.

11. The prosthetic implant as defined in claim 10, including a cap to at least partially cover said instrument cavity.

12. The prosthetic implant as defined in claim 8, wherein said at least one stabilizer includes a substance to at least partially inhibit tissue growth on said at least one stabilizer.

13. The prosthetic implant as defined in claim 4, wherein said at least one non-growth outer surface includes a substantially smooth surface.

14. The prosthetic implant as defined in claim 4, wherein said at least one non-growth outer surface includes a substantially non-smooth surface.

15. The prosthetic implant as defined in claim 3, wherein at least one opening includes a substance to at least partially inhibit tissue growth in said opening.

16. The prosthetic implant as defined in claim 3, including at least one stabilizer connected to and positioned at least partially about said exterior surface of said substantially spherical or ellipsoidal body, said at least one stabilizer at least partially limiting movement of said substantially spherical or ellipsoidal body between said adjoining vertebrae.

17. The prosthetic implant as defined in claim 1, wherein at least a portion of said at least one non-growth outer surface is formed by a coating material applied to at least a portion of said exterior surface of said substantially spherical or ellipsoidal body.

18. The prosthetic implant as defined in claim 17, wherein said coating material includes a substance to at least partially inhibit tissue growth on said coating material.

19. The prosthetic implant as defined in claim 1, wherein said at least one non-growth outer surface includes a substantially smooth surface.

20. The prosthetic implant as defined in claim 1, wherein said at least one non-growth outer surface includes a substantially non-smooth surface.

21. The prosthetic implant as defined in claim 1, including at least one stabilizer connected to and positioned at least partially about said exterior surface of said substantially spherical or ellipsoidal body, said at least one stabilizer at least partially limiting movement of said substantially spherical or ellipsoidal body between said adjoining vertebrae.

22. The prosthetic implant as defined in claim 21, wherein said at least one stabilizer is substantially disc shaped.

23. The prosthetic implant as defined in claim 21, wherein said at least one stabilizer includes a substance to at least partially inhibit tissue growth on said at least one stabilizer.

24. The prosthetic implant as defined in claim 21, wherein said at least one stabilizer includes a substance to at least partially promote tissue growth on said at least one stabilizer.

25. The prosthetic implant as defined in claim 1, including an instrument cavity adapted to receive an instrument to guide said prosthetic implant between adjoining vertebrae in a spinal column, to receive an implant to secure said prosthetic implant in position relative to said vertebrae, and combinations thereof.

26. The prosthetic implant as defined in claim 15, including a cap to at least partially cover said instrument cavity.

27. A prosthetic impart to at least partially support adjoining vertebrae in a spinal column, comprising a prosthetic implant having a substantially spherical or ellipsoidal body that includes an exterior surface, said exterior surface including at least one growth promoting outer area, said growth promoting outer area at least partially promoting tissue growth on said at least one growth promoting outer area while positioned between adjoining vertebrae, said at least one growth promoting outer area including a substantially smooth surface, said substantially spherical or ellipsoidal body being formed of a material designed to maintain a tension load of at least about ten pounds without substantially deforming, less than about 50% of the volume of said substantially spherical or ellipsoidal body constituting one or more cavities.

28. The prosthetic implant as defined in claim 27, wherein said at least one growth promoting outer area includes a substance that promotes tissue growth.

29. The prosthetic implant as defined in claim 28, wherein said at least one growth promoting outer area includes at least one opening that at least partially provides fluid access to at least one cavity in the interior of said substantially spherical or ellipsoidal body.

30. The prosthetic implant as defined in claim 29, wherein at least one of said at least one cavities has a substantially cylindrical shape.

31. The prosthetic implant as defined in claim 30, including an instrument cavity adapted to receive an instrument to guide said prosthetic implant between adjoining vertebrae in a spinal column, to receive an implant to secure said prosthetic implant in position relative to said vertebrae, and combinations thereof.

32. The prosthetic implant as defined in claim 31, including a cap to at least partially cover said instrument cavity.

33. The prosthetic implant as defined in claim 30, wherein at least a portion of said at least one growth promoting outer area is formed by a coating material applied to an outer surface of said substantially spherical or ellipsoidal body.

34. The prosthetic implant as defined in claim 33, wherein said coating material at least partially covers at least one opening in said outer surface of said substantially spherical or ellipsoidal body.

35. The prosthetic implant as defined in claim 33, wherein said coating material includes a substance to at least partially promote tissue growth on said exterior surface.

36. The prosthetic implant as defined in claim 30, wherein said at least one growth promoting outer area includes a substantially non-smooth surface.

37. The prosthetic implant as defined in claim 36, including at least one stabilizer positioned at least partially about said exterior surface of said substantially spherical or ellipsoidal body, said at least one stabilizer at least partially limiting movement of said body between said adjoining vertebrae.

38. The prosthetic implant as defined in claim 37, wherein said at least one stabilizer includes a substance to at least partially promote tissue growth on said at least one stabilizer.

39. The prosthetic implant as defined in claim 30, including at least one stabilizer positioned at least partially about said exterior surface of said substantially spherical or ellipsoidal body, said at least one stabilizer at least partially limiting movement of said body between said adjoining vertebrae.

40. The prosthetic implant as defined in claim 27, wherein said at least one growth promoting outer area includes at least one opening that at least partially provides fluid access to at least one cavity in the interior of said substantially spherical or ellipsoidal body.

41. The prosthetic implant as defined in claim 40, wherein at least one of said at least one cavities has a substantially cylindrical shape.

42. The prosthetic implant as defined in claim 27, including an instrument cavity adapted to receive an instrument to guide said prosthetic implant between adjoining vertebrae in a spinal column, to receive an implant to secure said prosthetic implant in position relative to said vertebrae, and combinations thereof.

43. The prosthetic implant as defined in claim 42, including a cap to at least partially cover said instrument cavity.

44. The prosthetic implant as defined in claim 27, wherein at least a portion of said at least one growth promoting outer area is formed by a coating material applied to an outer surface of said substantially spherical or ellipsoidal body.

45. The prosthetic implant as defined in claim 44, wherein said coating material at least partially covers at least one opening in said outer surface of said substantially spherical or ellipsoidal body.

46. The prosthetic implant as defined in claim 44, wherein said coating material includes a substance to at least partially promote tissue growth on said exterior surface.

47. The prosthetic implant as defined in claim 27, wherein said at least one growth promoting outer area includes a substantially non-smooth surface.

48. The prosthetic implant as defined in claim 27, including at least one stabilizer positioned at least partially about said exterior surface of said substantially spherical or ellipsoidal body, said at least one stabilizer at least partially limiting movement of said body between said adjoining vertebrae.

49. The prosthetic implant as defined in claim 48, wherein said at least one stabilizer is substantially disc shaped.

50. The prosthetic implant as defined in claim 48, wherein said at least one stabilizer includes a substance to at least partially promote tissue growth on said at least one stabilizer.

51. A prosthetic implant to at least partially support adjoining vertebrae in a spinal column, comprising a prosthetic implant having a substantially spherical or ellipsoidal body and at least one stabilizer positioned at least partially about an exterior surface of said substantially spherical or ellipsoidal body, said substantially spherical or ellipsoidal body being formed of a material designed to maintain a tension load of at least about ten pounds without substantially deforming, less than about 50% of the volume of said substantially spherical or ellipsoidal body constituting one or more cavities, said at least one stabilizer at least partially connected to said exterior surface of said substantially spherical or ellipsoidal body, said at least one stabilizer at least partially limiting the movement of said substantially spherical or ellipsoidal body between said adjoining vertebrae.

52. The prosthetic as defined in claim 51, wherein less than about 40% of the volume of said substantially spherical or ellipsoidal body constitutes one or more cavities.

53. The prosthetic implant as defined in claim 52, wherein less than about 30% of the volume of said substantially spherical or ellipsoidal body constitutes one or more cavities.

54. The prosthetic implant as defined in claim 53, wherein less than about 20% of the volume of said substantially spherical or ellipsoidal body constitutes one or more cavities.

55. The prosthetic implant as defined in claim 54, wherein less than about 10% of the volume of said substantially spherical or ellipsoidal body constitutes one or more cavities.

56. The prosthetic implant as defined in claim 55, said substantially spherical or ellipsoidal body includes substantially no cavities.

57. The prosthetic implant as defined in claim 51, wherein said at least one stabilizer is positioned completely about said exterior surface of said substantially spherical or ellipsoidal body.

58. The prosthetic implant as defined in claim 57, wherein said at least one stabilizer is positioned substantially about a central axis of said substantially spherical or ellipsoidal body.

59. The prosthetic implant as defined in claim 58, wherein said at least one stabilizer is substantially disc shaped.

60. The prosthetic implant as defined in claim 59, wherein said at least one stabilizer has a maximum radial width, said maximum radial width being less than about one times a maximum radius of said substantially spherical or ellipsoidal body.

61. The prosthetic implant as defined in claim 60, wherein said at least one stabilizer has a maximum thickness, said maximum thickness being less than about 1.5 times the maximum diameter of said substantially spherical or ellipsoidal body.

62. The prosthetic implant as defined in claim 61, wherein said at least one stabilizer has a thickness at least closely adjacent to said substantially spherical or ellipsoidal body that is greater than a maximum thickness of an outer edge of said at least one stabilizer.

63. The prosthetic implant as defined in claim 62, wherein said thickness of said at least one stabilizer reduces at a generally constant rate from at least closely adjacent to said substantially spherical or ellipsoidal body to said outer edge of said at least one stabilizer.

64. The prosthetic implant as defined in claim 63, wherein said at least one stabilizer and said substantially spherical or ellipsoidal body are formed from substantially the same material.

65. The prosthetic implant as defined in claim 64, wherein said body is substantially spherical.

66. The prosthetic implant as defined in claim 51, wherein said at least one stabilizer is positioned substantially about a central axis of said substantially spherical or ellipsoidal body.

67. The prosthetic implant as defined in claim 51, wherein said at least one stabilizer is substantially disc shaped.

68. The prosthetic implant as defined in claim 51, wherein said at least one stabilizer includes at least one tapered edge.

69. The prosthetic implant as defined in claim 51, wherein said at least one stabilizer includes a substance to at least partially promote tissue growth on said at least one stabilizer.

70. The prosthetic implant as defined in claim 51, wherein said at least one stabilizer includes a substance to at least partially prevent tissue growth on said at least one stabilizer.

71. The prosthetic implant as defined in claim 51, wherein said at least one stabilizer includes a substance selected from the group consisting of medicine, human tissue, animal tissue, synthetic tissue, human cells, animal cells, synthetic cells, bone activating matter, and combinations thereof.

72. The prosthetic implant as defined in claim 51, wherein said at least one stabilizer includes a substantially smooth surface.

73. The prosthetic implant as defined in claim 51, wherein said at least one stabilizer does not include an opening.

74. The prosthetic implant as defined in claim 51, wherein said at least one stabilizer has a maximum radial width, said maximum radial width being less than about three times a maximum radius of said substantially spherical or ellipsoidal body.

75. The prosthetic implant as defined in claim 74, wherein said at least one stabilizer has a maximum radial width, said maximum radial width being less than about two times a maximum radius of said substantially spherical or ellipsoidal body.

76. The prosthetic implant as defined in claim 75, wherein said at least one stabilizer has a maximum radial width, said maximum radial width being less than about one times a maximum radius of said substantially spherical or ellipsoidal body.

77. The prosthetic implant as defined in claim 51, wherein said at least one stabilizer has a maximum thickness, said maximum thickness being less than a maximum diameter of said substantially spherical or ellipsoidal body.

78. The prosthetic implant as defined in claim 77, wherein said at least one stabilizer has a maximum thickness, said maximum thickness being less than about 1.5 times the maximum diameter of said substantially spherical or ellipsoidal body.

79. The prosthetic implant as defined in claim 78, wherein said at least one stabilizer has a maximum thickness, said maximum thickness being less than about 4 times the maximum diameter of said substantially spherical or ellipsoidal body.

80. The prosthetic implant as defined in claim 51, wherein said at least one stabilizer has a thickness at least closely adjacent to said substantially spherical or ellipsoidal body that is greater than a maximum thickness of an outer edge of said at least one stabilizer.

81. The prosthetic implant as defined in claim 80, wherein said thickness of said at least one stabilizer reduces at a generally constant rate from at least closely adjacent to said substantially spherical or ellipsoidal body to said outer edge of said at least one stabilizer.

82. The prosthetic implant as defined in claim 51, wherein said at least one stabilizer and said substantially spherical or ellipsoidal body are formed from substantially the same material.

83. The prosthetic implant as defined in claim 51, wherein said exterior surface includes at least one non-growth surface area.

84. The prosthetic implant as defined in claim 83, wherein at least a portion of said at least one non-growth surface area is formed by a coating material.

85. The prosthetic implant as defined in claim 83, wherein said at least one non-growth surface area includes a substantially smooth surface.

86. The prosthetic implant as defined in claim 51, wherein said exterior surface includes at least one growth surface area.

87. The prosthetic implant as defined in claim 86, wherein at least a portion of said at least one growth surface area is formed by a coating material.

88. The prosthetic implant as defined in claim 86, wherein said at least one growth surface area includes a substantially smooth surface.

89. The prosthetic implant as defined in claim 51, wherein said body is substantially spherical.

* * * * *